United States Patent [19]

Etzel

[11] 4,288,430
[45] Sep. 8, 1981

[54] DISINFECTANT CHLORINATED CYANURATE CONTAINING COMPOSITIONS AND METHOD OF USE

[75] Inventor: James E. Etzel, Lafayette, Ind.

[73] Assignee: Purdue Research Foundation, Lafayette, Ind.

[21] Appl. No.: 64,346

[22] Filed: Aug. 6, 1979

[51] Int. Cl.³ .................. A01N 59/08; A01N 43/64
[52] U.S. Cl. ................................. 424/153; 424/249
[58] Field of Search ............................. 424/153, 249

[56] References Cited

U.S. PATENT DOCUMENTS

| | | | |
|---|---|---|---|
| 3,072,654 | 1/1963 | Uazopolos | 424/249 |
| 3,272,813 | 9/1966 | Symes | 424/249 |
| 3,853,867 | 12/1974 | Berkowitz et al. | 424/249 |
| 3,956,444 | 5/1976 | Kibbel | 424/249 |

FOREIGN PATENT DOCUMENTS 1437925  6/1976  United Kingdom ............... 424/249

OTHER PUBLICATIONS

Chem. Abst. 74, 130245X, (1971), Molozhavaya.
Chem. Abst. 83, 15404X, (1975)–Veger.

*Primary Examiner*—Douglas W. Robinson
*Attorney, Agent, or Firm*—Biebel, French & Nauman

[57] ABSTRACT

A disinfectant composition for use in water conditioning systems is produced by dry mixing sodium chloride and a chlorinated cyanurate and pelletizing the mixture. The composition releases free chlorine to disinfect brine solutions used in regenerating domestic water conditioning ion exchange columns and prevents bacterial contamination of such columns.

2 Claims, No Drawings

DISINFECTANT CHLORINATED CYANURATE CONTAINING COMPOSITIONS AND METHOD OF USE

BACKGROUND OF THE INVENTION

This invention relates to disinfectant compositions, and more particularly to a pelletized disinfectant salt composition for use in water softening systems.

Disinfection of domestic water supplies in the United States by chlorination has been practiced since the late 1800's. Early methods utilized chlorinated lime, sodium and calcium hypochlorite, or chlorine gas added to water systems at a central location. The use of chlorinated cyanurates as a convenient source of available chlorine for bleaching and disinfectant purposes has also been popular for several years. These organic compounds, generally classified as chloramines, contain chlorine bearing nitrogen atoms located between a pair of carbonyl (C=O) groups and have been found to exhibit good stability as well as bactericidal properties in water.

In recent years, the increasing numbers of backyard swimming pools has created a need for disinfecting compositions which are added directly to the water by the individual consumer. Both hypochlorite and chlorinated cyanurate compounds have found use in swimming pools as disinfectants. See, for example, Hilton, "The Chlorinated Cyanurates", *Swimming Pool Age*, Nov. 1961.

In European countries, there has been a recognition of the problem of possible bacterial growth in brine solutions used to regenerate water conditioning systems. Bacterial growth in such solutions could contaminate domestic drinking water supplies if bacteria remained in the ion exchange resin column after a regeneration cycle. Efforts have been made in Europe to combat this problem by treating the ion exchange columns after each regeneration cycle with chemicals or in some cases with silver impregnated resins that have been dispersed into such columns. However, chloramine compounds, one of the chemicals used, do not react rapidly and require contact times of at least two hours to disinfect effectively a water supply. See, W. Hardenbergh, Water Supply and Purification 413 (1952). Such long contact times are impractical for domestic water conditioning systems since the ion exchange resin would be unavailable to perform its softening function for extended time periods. Use of silver impregnated ion exchange resins in the resin column likewise is impractical because of the high cost of such resins and the ineffectiveness of silver compounds in disinfecting water supplies. Id. at 416.

Accordingly, the need exists in the field of domestic water conditioning for a means to disinfect effectively brine solutions used for regeneration of ion exchange resins thus avoiding contamination of such resins and resulting in a minimum of time for which the water conditioning unit is unavailable to perform its softening function.

SUMMARY OF THE INVENTION

In accordance with the present invention, a disinfectant composition is compounded with sodium chloride, and the mixture is formed into pellets. The disinfectant pellets can then be added to the brine storage tank of a conventional domestic water conditioning system. As brine solution is formed at the bottom of the storage tank by dissolving the pellets in water, chlorine disinfectant is released from the pellets to control effectively any bacterial growth in the solution. There is, therefore, no danger of bacterial contamination of the ion exchange column during regeneration with such brine solutions.

As the disinfectant agent, various chloramine compounds can be utilized. Desirable properties for such compounds include high available chlorine content, solid crystalline form for ease of pelletizing, rapid solubility in water, stability in dry formulation, nontoxic to humans at low concentrations, and no calcium ion contamination. It has been found that chlorinated cyanurate compounds such as potassium dichloroisocyanurate (1-potassium, 3,5-dichloro-s-triazine-2,4,6-trione) and sodium dichloroisocyanurate (1-sodium, 3,5-dichloro-s-triazine-2,4,6-trione) are particularly useful and possess all of the above properties.

The disinfectant pellets are formed by mixing a small, predetermined amount of a dry powdered cyanurate compound with fine grain crystalline salt (i.e., sodium chloride or other regenerant salt). The mixture may then be compressed into pellets using a conventional pill press. It has been found that by using a ratio in the range of $6.5 \times 10^{-3}$ grams of potassium dichloroisocyanurate to about one gram of salt, sufficient residual chlorine will be released into the brine solution to insure bactericidal effectiveness over extended periods of time.

Accordingly, it is an object of this invention to provide an inexpensive, convenient to use, and effective means of disinfecting brine solutions in domestic water conditioning systems and thereby avoid contamination of the ion exchange column during regeneration. This and other objects and advantages of the invention will become apparent from the following description and appended claims.

DESCRIPTION OF THE PREFERRED EMBODIMENTS

Figure 1:
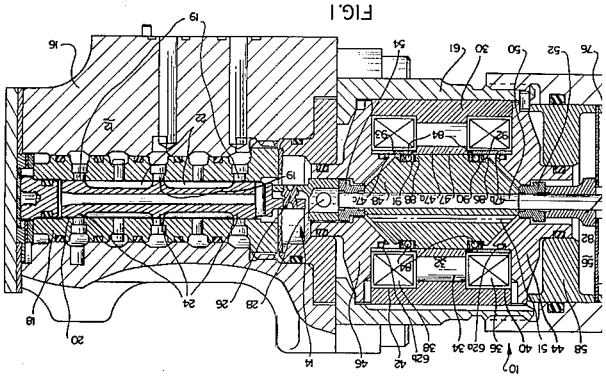

Chlorinated cyanurates have been used safely as sources of available chlorine for bleaching and disinfectant purposes for several years. They are, therefore, known to be effective in controlling the growth of bacteria. Their use in swimming pools as a source of chlorine has also shown them to present no toxicological problems to humans. The preferred chlorinated cyanurates for use in this invention are potassium dichloroisocyanurate (1-potassium-3,5-dichloro-s-triazine-2,4,6-trione) and sodium dichloroisocyanurate (1-sodium-3,5-dichloro-s-triazine-2,4,6-trione). They are available from Monsanto Chemical Company, St. Louis, Missouri, under the trademarks ACL-59 and ACL-60, respectively. It has been found that these compounds exhibit the physical properties required for use as disinfectants in brine storage tanks. The compounds have a high percentage of available chlorine, they have a solid crystalline form and rapidly dissolve in water, and they are stable when dry mixed with sodium chloride.

The chlorinated cyanurates can be mixed easily with fine grain sodium chloride and then pelletized by using a conventional pellet mill or pill press. It was found that moderate pressures (up to 50,000 psi) were sufficient to form the granular mixture into compact pellets. The size and shape of the pellets are not critical, with the major consideration being the ease of handling of the pellets. Pellets having diameters of from $\frac{1}{4}''$ to $\frac{1}{2}''$ and having generally spherical or flattened pill shapes are preferred.

It has been found that the addition of as little as 1 to 3 ppm (mg/l) of dichloroisocyanurate compound produces a very high initial kill rate of bacteria which greatly reduced the bacteria even after 96 hours. Addition of 3 ppm and above of dichloroisocyanurate to a water system should provide both a high initial kill rate as well as sufficient residual chlorine to maintain an essentially bacteria-free environment.

However, to establish the effectiveness of such known disinfectants in term of the present invention, a series of tests were run to check the effect of brine solution and moist air on the residual levels of chlorine produced with the disinfectant chemicals and the ability of the pelletized composition to maintain a sufficient level of residual chlorine in a brine storage tank environment. The results were as reported in the following examples.

EXAMPLE I

The effects of brine solution and humidity on residual chlorine produced by cyanurate compounds were tested. Deionized water was saturated with sodium chloride at room temperature. Potassium dichloroisocyanurate was then added to the saturated solution at a ratio of 100 mg cyanurate to one liter of solution. The starch-iodide method was used to determine residual chlorine content. Samples were taken and tested at several intervals. The results are reported in Table I below.

TABLE I

| Residual Chlorine (mg/l) | Time |
|---|---|
| 446 | 0 (at mixing) |
| 465 | 30 minutes |
| 436 | 1 hour |
| 195 | 8.5 days |

The results show that the maximum level of residual chlorine occurred shortly after mixing and that the level then dropped over a period of several days. A significant level of residual chlorine remained in the test solution even after 8.5 days, indicating that brine has no drastic effect on the residual chlorine level produced by cyanurate compounds.

Fresh, dry potassium dichloroisocyanurate was tested against cyanurate which had been exposed to the ambient air for three days to determine if moisture in the air significantly affected the stability or ability of the compound to release free chlorine. To test this, 2000 mg/l of potassium dichloroisocyanurate (both fresh and aged 3 days) was added to one liter of deionized water. Samples were taken at 30 minute intervals. The results are reported in Table II below.

TABLE II

| | Residual Chlorine | |
|---|---|---|
| Time (min.) | Fresh (mg/l) | Aged (mg/l) |
| 0 | 844 | 864 |
| 30 | 909 | 896 |
| 60 | 866 | 905 |

The results indicate that the cyanurate compound remains stable upon exposure to the ambient atmosphere and that moisture in the air has no significant effect on the ability of the compound to release free chlorine in solution.

EXAMPLE II

The tests in this example were designed to determine the disinfection potential of salt and potassium dichloroisocyanurate pellets in a simulated brine storage tank environment. The experiment was carried out over a three-month period to insure that the pellets would not be degraded over a reasonable period of time such as would be required for a given charge of pellets to be used by a domestic water conditioning system.

Fine grain crystalline sodium chloride and powdered potassium dichloroisocyanurate were mixed together in a ratio of about $6.5 \times 10^{-3}$ grams of cyanurate to one gram of salt. The mixture was fed to a three-eighths inch diameter pill press where it was formed into pellets.

Two 4.4 cm diameter glass columns were constructed and sealed at the bottom with one hole rubber stoppers. Tubing from the stoppers was clamped shut when water was not being added to or removed from the column. Disinfectant pellets were added to the columns maintaining a ratio of 36" of pellets for every 6" to 8" of water. Brine solution was removed every third day for testing of the level of residual chlorine by the starch iodide method. Fresh deionized water was introduced to replace the brine. The tops of the columns were loosely covered to keep out contaminants but permit air circulation. The results are reported in Tables III and IV below.

TABLE III

| Column No. | Inches of Pellets | No. of Pellets | Water Height (in.) |
|---|---|---|---|
| 1 | 30 | 690 | 5.84 |
| 2 | 23 | 530 | 4.50 |

TABLE IV

| Residual Chlorine | | |
|---|---|---|
| Column #1 mg/l | Column #2 mg/l | Time Elapsed days |
| 3880.0 | 3150 | 3 |
| 854.0 | 990 | 6 |
| 1870.0 | 801 | 9 |
| 970.0 | 801 | 12 |
| 100.0 | 826 | 15 |
| 800.0 | 740 | 40 |
| 130.0 | 170 | 43 |
| 25.3 | 287 | 46 |
| 14.4 | 1280 | 49 |
| 400.0 | 485 | 52 |
| 885.0 | 362 | 55 |
| 312.0 | 668 | 59 |
| 550.0 | 20 | 62 |
| 296.0 | 366 | 65 |
| 866.0 | 1188 | 68 |
| 524.0 | 1184 | 72 |
| 322.0 | 868 | 75 |
| 595.0 | 616 | 78 |
| 154.0 | 275 | 81 |
| 1120.0 | 482 | 84 |
| 380.0 | 790 | 87 |
| 121.0 | 1015 | 90 |
| 1036.0 | 504 | 93 |
| Average 658.0 mg/l | 777 mg/l | |

As can be seen from Table IV, there was substantial variation in the measured residual chlorine levels. This can be explained partly by the visually observed phenomenon of hanging up of the pellets in the small diam- IMAGE SYSTEM
TEST TARGET
A
U.S. DEPARTMENT OF COMMERCE
PATENT AND TRADEMARK OFFICE